United States Patent [19]

Itoh et al.

[11] Patent Number: 4,743,595

[45] Date of Patent: May 10, 1988

[54] PROCESS FOR PREPARING 2-AMINO-5-NITROPHENOL DERIVATIVES

[75] Inventors: Isamu Itoh; Mitsunori Ono; Hidetoshi Kobayashi; Kazuyoshi Yamakawa, all of Minami-ashigara, Japan

[73] Assignee: Fuji Photo Film Co., Ltd., Kanagawa, Japan

[21] Appl. No.: 743,956

[22] Filed: Jun. 12, 1985

[30] Foreign Application Priority Data

Jun. 14, 1984 [JP] Japan ................. 59-122460

[51] Int. Cl.$^4$ ............... C07C 149/42; C07C 87/60; C07C 91/40; C07C 103/87

[52] U.S. Cl. .................... 544/111; 544/138; 544/365; 544/377; 546/192; 546/226; 546/233; 546/237; 548/256; 548/261; 548/336; 548/518; 548/525; 549/472; 549/487; 549/504; 549/505; 564/45; 564/46; 564/51; 564/52; 564/57; 564/155; 564/164; 564/165; 564/168; 564/169; 564/174; 564/185; 564/186; 564/187; 564/192; 564/197; 564/200; 564/207; 564/220; 564/227; 564/413

[58] Field of Search ............ 564/413, 45, 46, 51, 564/52, 53, 56, 57, 155, 161, 165, 166, 168, 169, 185, 186, 187, 192, 195, 197, 200, 207, 213, 220, 222; 568/638, 635; 544/111, 132, 138, 368, 377; 546/197, 198, 226, 229, 233, 237, 270, 273, 275, 217, 219, 237; 548/256, 257, 261, 336, 347, 518, 523, 525, 530, 579, 964; 594/472, 487, 504, 505

[56] References Cited

U.S. PATENT DOCUMENTS

| | | | |
|---|---|---|---|
| 2,296,200 | 10/1981 | Yagihara et al. | 430/551 |
| 3,476,563 | 11/1969 | Loria | 430/553 |
| 3,617,291 | 11/1971 | Sawdey | 430/553 |
| 3,880,661 | 4/1975 | Lau et al. | 430/384 |
| 3,912,606 | 10/1975 | Pacifici et al. | 564/413 |
| 4,052,212 | 10/1977 | Deguchi et al. | 430/385 |
| 4,124,396 | 11/1978 | Osborn | 430/553 |
| 4,264,769 | 4/1981 | Förster | 568/638 |
| 4,296,199 | 10/1981 | Yagihara et al. | 430/551 |
| 4,299,914 | 11/1981 | Fujimatsu et al. | 430/384 |
| 4,304,844 | 12/1981 | Fujimatsu et al. | 430/384 |
| 4,310,693 | 1/1982 | Fujita et al. | 564/222 |
| 4,333,999 | 6/1982 | Lau | 430/17 |
| 4,341,864 | 7/1982 | Vandewalle et al. | 430/505 |
| 4,377,712 | 3/1983 | Foster et al. | 568/635 |
| 4,427,767 | 1/1984 | Aoki et al. | 430/552 |
| 4,463,086 | 7/1984 | Sasaki et al. | 430/553 |
| 4,465,766 | 8/1984 | Sato et al. | 430/552 |
| 4,579,813 | 4/1986 | Aoki et al. | 430/505 |

FOREIGN PATENT DOCUMENTS

| | | | |
|---|---|---|---|
| 153923 | 12/1977 | Japan | 430/551 |
| 110530 | 4/1978 | Japan | 430/551 |
| 32071 | 3/1980 | Japan | 430/551 |
| 153775 | 11/1980 | Japan | 430/551 |
| 163537 | 12/1980 | Japan | 430/551 |
| 1938 | 1/1981 | Japan | 430/551 |
| 29235 | 3/1981 | Japan | 430/551 |
| 27147 | 3/1981 | Japan | 430/551 |
| 55945 | 5/1981 | Japan | 430/551 |
| 100771 | 8/1981 | Japan | 430/551 |
| 204543 | 12/1982 | Japan | 430/551 |
| 204544 | 12/1982 | Japan | 430/551 |
| 204545 | 12/1982 | Japan | 430/551 |
| 158470 | 8/1983 | Japan | 430/551 |
| 157424 | 8/1983 | Japan | 430/551 |
| 145333 | 8/1983 | Japan | 430/551 |
| 157423 | 8/1983 | Japan | 430/551 |
| 199696 | 10/1983 | Japan | 430/551 |
| 31953 | 2/1984 | Japan | 430/551 |
| 31954 | 2/1984 | Japan | 430/551 |
| 7910 | of 1905 | United Kingdom | 564/413 |
| 647209 | 12/1950 | United Kingdom | 564/413 |
| 2067559 | 7/1981 | United Kingdom | 430/551 |

OTHER PUBLICATIONS

The "Element Effect" as a Criterion of Mechanism in Activated Aromatic Nucleophilic Substitution Reactions by J. E. Bunnett et al., pp. 385–391.

Chapter 13, entitled "Aromatic Nucleophilic Substitution", pp. 584–595.

Primary Examiner—Richard L. Raymond
Assistant Examiner—Raymond Covington
Attorney, Agent, or Firm—Birch, Stewart, Kolasch & Birch

[57] ABSTRACT

A process for efficiently preparing 2-amino-5-nitrophenol derivatives in which benzoxazole derivatives are subjected to nucleophilic substitution reaction at the 5 position thereof to obtain corresponding benzoxazole derivatives, and the oxazole ring of the benzoxazole derivatives is then subjected to ring-opening to obtain 2-amino-5-nitrophenol derivatives. The 2-amino-5-nitrophenol derivatives are useful as industrial starting materials, reducing agents or antioxidants and intermediates for cyan-image-forming couplers.

17 Claims, No Drawings

PROCESS FOR PREPARING 2-AMINO-5-NITROPHENOL DERIVATIVES

BACKGROUND OF THE INVENTION

1. Field of the Invention

This invention relates to a process for preparing 2-amino-5-nitrophenol derivatives and more particularly, to a process for preparing 2-amino-5-nitrophenol derivatives in which an appropriate nucleophilic group is introduced at the 4 position of the derivative.

2. Description of the Prior Art

2-Amino-5-nitrophenol derivatives are generalpurpose compounds for use as industrial starting materials, and can be converted into synthetic intermediates of higher added value by the reduction of the nitro group. The compounds have the o-aminophenol structure which may serve as a reducing agent, and the degree of reducibility can be arbitrarily controlled by the introduction of a suitable substituent and the conversion of the nitro group into another functional group. In this sense, the derivatives are important as diversity of reducing agents or antioxidants or synthetic intermediates which are convertible into physiologically active compounds by the modification of the nitrogen atom.

Moreover, 2-amino-5-nitrophenol derivatives are also important as synthetic intermediates for cyan-imageforming couplers in the field of photographic chemistry. In recent years, it has been found that 2,5-diacylaminophenol cyan-couplers show good color restoration upon development and the resulting dyes have good fastness to heat and/or humidity (see, for example, Japanese Patent Application (OPI) Nos. 110530/78, 163537/80, 29235/81, 55945/81, 31953/84 and 31954/84, and U.S. Pat. Nos. 4,124,396 and 4,341,864). It has been also found that dyes produced from 2-phenylureido-5-acylaminophenol cyancouplers are excellent in color restoration upon development, absorption wavelength, and fastness to heat and/or humidity (see, for example, U.S. Pat. Nos. 4,333,999 and 4,427,767 and Japanese Patent Application (OPI) Nos. 204543/82, 204544/82 and 204545/82). Accordingly, 2-amino-5-nitrophenol derivatives have attracted attention for use as synthetic intermediates for those couplers.

Photographic couplers may be broadly classified with respect to the hue of developed dye. They may also be stoichiometrically classified into two broad classes, i.e. 2-equivalent couplers and 4-equivalent couplers. While 4-equivalent couplers require four moles of silver halide to be developed into one mole of dye, 2-equivalent couplers have a split-off group at the coupling position thereof and can form one mole of dye using two moles of silver halide. For this reason, it is known that 2-equivalent couplers are more beneficial from the standpoint of silver saving. With regard to cyan-developing couplers, for instance, 2-equivalent couplers have such a high colordeveloping speed that photographic senistivity is much improved (see, for example, U.S. Pat. Nos. 3,476,563, 3,617,291, 3,880,661, 4,052,212 and British Patent Nos. 1,531,927 and 2,006,755, and Japanese Patent Application (OPI) Nos. 32071/80, 1938/81 and 27147/81).

As recent color negative films increase in sensitivity, 2-equivalent couplers of high color developing speed, in which split-off groups are introduced at the coupling position, have been employed in large amounts. Accordingly, of increasing importance are 2-amino-5-nitrophenol derivatives and processes for preparing such derivatives.

As explained above, 2-amino-5-nitrophenol derivatives in which substituents are introduced into the benzene ring are important as industrial starting materials, reducing agents, and intermediates for preparing cyan couplers in photographic chemistry. Preparation of these derivatives is described, for example, in U.S. Pat. No. 3,880,661, and Japanese Patent Application Nos. 145333/83, 157423/83, 158470/83, 157424/83, and 199,696/83. One such example may be represented by the following reaction formula (a)

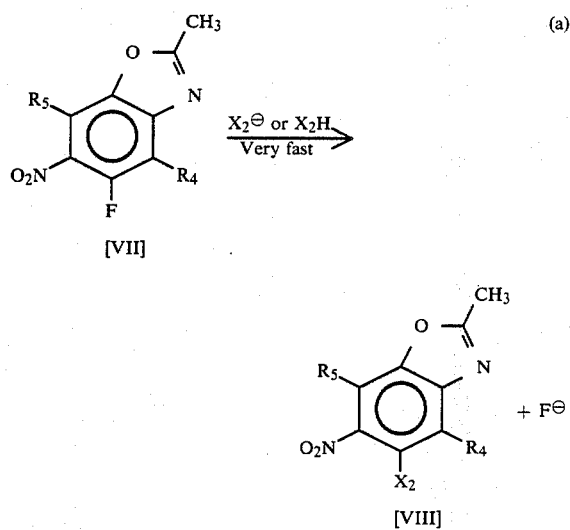

wherein $R_4$ and $R_5$ each represents a hydrogen atom or a substituent, and $X_2$ represents a nucleophilic group.

The above substitution reaction per se is known as an aromatic nucleophilic substitution reaction. This reaction is described in detail, for example, in Jerry March "Advanced Organic Chemistry" (second edition, (1977), Mcgraw-Hill Kogakusha, Ltd.), chapter 13 entitled "Aromatic Nucleophilic Substitution" pp. 584–595. In the Journal of American Chemical Society, Vol. 79, p. 385 (1957), J. F. Bunnet et al report that the reaction between 2,4-dinitrobenzene derivatives and pyridine proceeds about 3300 times more rapidly when the split-off group is a fluorine atom than when the split-off group is a chlorine or bromine atom.

However, the conventional processes of synthesis, as exemplified as formula (a), have a number of disadvantages.

(1) The fluoro derivative of the general formula [VII], used as the starting material, is obtained by five steps starting from p-fluorophenol and is thus complicated in the preparation steps.

(2) The starting p-fluorophenol is not readily available and is expensive.

(3) Because fluorine ions are generated by the reaction, additional plant investment is necessary for safety and waste water disposal.

(4) The type of material for reactors is limited.

These disadvantages place a serious limitation on mass production. On the other hand, in order to overcome the above disadvantages, it is a matter of course that the reaction is effected using, instead of fluoro derivatives of general formula [VII], chloro derivatives of the following formula [IX] as described in U.S. Pat. No. 3,880,661

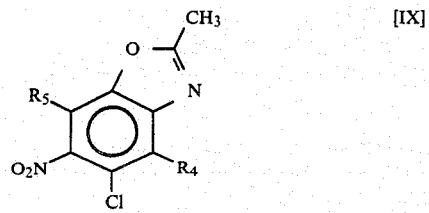

wherein R₄ and R₅ each has the same meaning as defined in formula (a), respectively. These chloro derivatives are prepared from 4-chloroaminophenol which are inexpensively available in large amounts. As expected, however, the chloro derivatives are much less reactive than fluoro derivatives [VII], thereby giving low yields. Even though the reaction is carried out in the presence of a catalyst such as Cu, CuI, CuI₂, CuCl₂, CuBr₂, CuO (Ullmann reaction, Fanta, *Synthesis*, 9, 12, 1974), the yield of desired product [VIII] is about 7% in a maximum with the balance of by-products with identified structures.

SUMMARY OF THE INVENTION

The present invention intends to provide a process for preparing 2-amino-5-nitrophenol derivatives which comprises subjecting a substituent of a benzoxazole derivative at the 5 position to nucleophilic substitution reaction to obtain a corresponding benzoxazole derivative, and further subjecting the thus obtained derivative to ring-opening reaction of the oxazole ring to obtain a 2-amino-5-nitrophenol derivative which has been introduced with a nucleophilic reagent or group at the 4 position.

It is a primary object of the present invention to provide a process for preparing 2-amino-5-nitrophenol derivatives, into which various nucleophilic groups are introduced at the 4 position, from inexpensive, readily available starting materials.

It is another object of the invention to provide a process for preparing 2-amino-5-nitrophenol derivatives, introduced with various nucleophilic groups at the 4 position thereof, which needs no additional steps such as treatment of fluorine ion-containing waste water and can be safely performed using conventional equipment.

It is a further object of the invention to provide a process for preparing 2-amino-5-nitrophenol derivatives, introduced with various nucleophilic groups at the 4 position, by a reduced number of steps in high yields.

It is a still further object of the invention to provide a process for preparing 2-amino-5-nitrophenol derivatives in which production cost is reduced.

Other and further objects, features and advantages of the invention will appear more fully from the following description.

DETAILED DESCRIPTION OF THE INVENTION

As a result of extensive studies it has been found that the 2-methyl group of the above-described chloro derivatives [IX] gave a great influence on the substitution reaction and that when the 2-methyl group is replaced by a group other than a primary alkyl group or a primary or secondary amino group, e.g. a secondary alkyl group, a tertiary alkyl group, an aryl group, a heterocyclic residue or a tertiary amino group, the substitution reaction with $X_2^\ominus$ or $X_2H$ proceeds smoothly with an intended substituted product being obtained in yields as high as 80% or more. Thus, the drawbacks involved in the case using fluoro derivatives [VII] could be fully overcome. The present invention is accomplished based on the above findings.

According to the invention, there is provided a process for preparing 2-amino-5-nitrophenol derivatives which comprise the steps of (1) subjecting a benzoxazole derivative of the following formula [I] to nucleophilic substitution reaction at the 5 position of the derivative

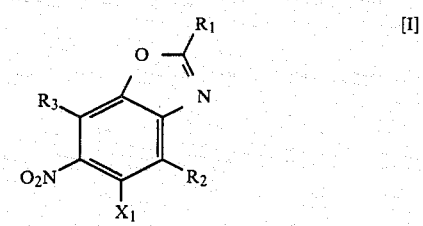

wherein $R_1$ represents a group bonding through a carbon atom having the number of substitution of hydrogen atoms of 1 or 0, or a group bonding through a hydrogen-free nitrogen atom, $R_2$ and $R_3$ each independently represents a hydrogen atom or a group replaceable to an aromatic ring, and $X_1$ represents a chlorine or bromine atom, and (2) opening the oxazole ring to obtain a 2-amino-5-nitrophenol derivative of the following formula [II]

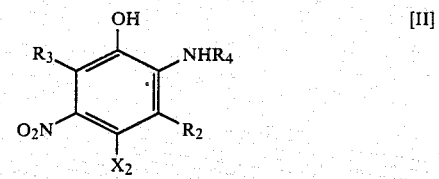

wherein $R_2$ and $R_3$ each has the same meaning as defined above, $R_4$ represents a hydrogen atom or a —COR₁ group which $R_1$ has the same meaning as defined above, and $X_2$ represents a nucleophilic group.

In accordance with the process of the invention, there is obtained a compound of general formula [III] by aromatic nucleophilic substitution reaction of the benzoxazole derivative of general formula [I]

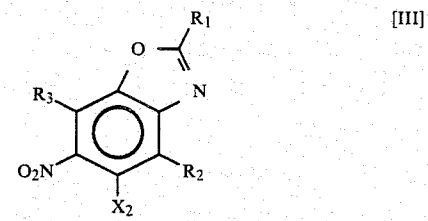

wherein $R_1$, $R_2$, $R_3$ and $X_2$ have the same meanings as defined above, respectively.

The compounds of general formula [I], [II] and [III] may be explained as follows. More specific examples will be summarized in Tables 1-3 appearing hereinafter.

In formulae [I], [II] and [III], when $R_1$ is a group bonded through a carbon atom having the number of substitution of hydrogen atoms of 1 or 0, $R_1$ preferably represents an aryl group, a heterocyclic residue, an alkenyl group, an alkynyl, a tertiary alkyl group, a secondary alkyl group, an acyl group, a carboxyl group and a ketimine group. When $R_1$ represents a di-substituted amino group wherein these substituents together may form a ring, preferred substituents bonded to the nitrogen atom of the amino group include an alkyl group, an alkenyl group, an aryl group, an acyl group, a sulfonyl group, and a heterocyclic group. These groups may be bonded to form a ring. Preferable groups as $R_1$ include such moieties that form bisbenzoxazole derivatives. These groups represented by $R_1$ may be further substituted by various substituents. Preferable substituents include a halogen atom, a hydroxyl group, an alkoxy group, an aryloxy group, a heterocyclic oxy group, an acyloxy group, an alkyl group, an alkenyl group, an alkynyl group, an aryl group, an amino group, a hydroxylamino group, a carbonamido group, a sulfonamido group, a ureido group, a sulfamido group, an oxycarbonamido group, a carboxyl group, a carbamoyl group, an oxycarbonyl group, a hydroxyaminocarbonyl group, a sulfo group, a sulfamoyl group, a hydroxyaminosulfamoyl group, an alkylsulfonyl group, an arylsulfonyl group, a cyano group, a nitro group, and a heterocyclic residue.

The groups represented by $R_2$ and $R_3$ in general formulae [I] through [III] may be the same or different. Preferable examples of the groups include a hydrogen atom, a halogen atom, an alkyl group, an alkenyl group, an aryl group, an alkoxy group, an aryloxy group, an acyloxy group, an amido group, a sulfonamido group, a ureido group, an alkyloxycarbonyl group, a carbamoyl group, a sulfamoyl group, a sulfonyl group, a sulfo group, a cyano group, and a heterocyclic residue. These groups may be further substituted.

$X_2$ in general formulae [II] and [III] represents all groups which have nucleophilicity and which can be produced by the nucleophilic substitution reaction with chlorine or bromine atom of the compound of general formula [I]. Preferably, nucleophilic groups having a hetero atom as the nucleophilic center are used. Specific examples of $X_2$ include fluorine, a hydroxyl group, an alkoxy group, an aryloxy group, a heterocyclic oxy group, an iminoxy group, an amidoxy group, a sulfonamidoxy group, an acyloxy group, a carbamoyloxy group, a sulfamoyloxy group, a cyanoxy group, an amino group, a carbonamido group, a sulfonamido, a ureido group, a sulfamido group, a hydroxylamino group, an imido group, an azido group, a heterocyclic residue, an alkylthio, an arylthio, a heterocyclic thio group, a cyanothio group, a sulfo group, a sulfothio group, an alkylsulfonyl group, an arylsulfonyl group, a heterocyclic sulfonyl group, an acylthio group, a thiocarbonylthio group, a cyano group, and a methyl group substituted with an electron attractive group. These groups may be further substituted.

Among the nucleophilic groups listed above, more preferable examples are aryloxy, heterocyclic oxy, heterocyclic residue, arylthio and heterocyclic thio group and the most preferable example is aryloxy group.

The process of the invention may be represented by the following sequence of reactions including preparation of benzoxazole derivatives of general formula [I].

[Reaction Scheme]

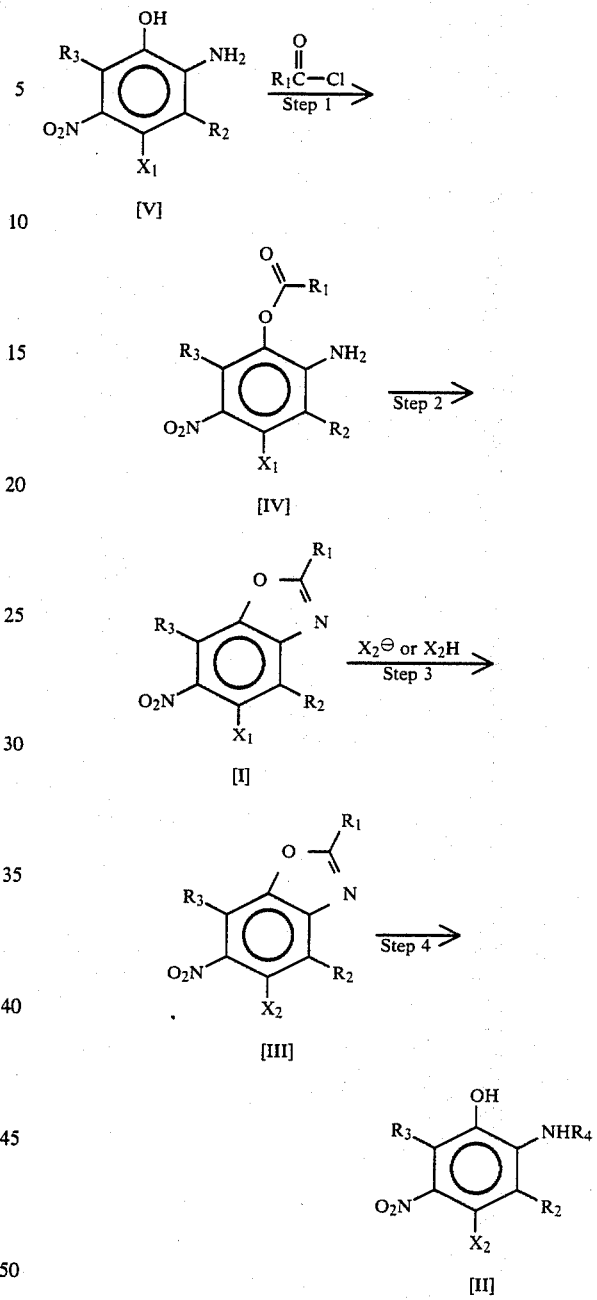

The above reaction schemes are described in more detail hereinabove.

[Step 1]

Preparation of compound [IV] from aminophenol derivative [V] is achieved by reaction with $R_1COCl$ in the presence of a strong organic base. Preferable examples of the organic base include triethylamine, 1,4-diazabicyclooctane, diazabicycloundecene, diazabicyclononene, 4-(N,N-dimethyl)pyridine and the like. In general, the hydroxyl group is less reactive with acid chlorides than the amino group. However, if the strong base is present, the oxygen atom alone takes part in the reaction, thereby selectively producing compound [IV]. If the above reaction is carried out in the presence of weak bases such as, for example pyridine, the intended compound [IV] is scarcely obtained but the resulting product is a compound obtained by reaction with the amino group. Thus, the reaction between the compound [V] and $R_1COCl$ varies depending on the type of base, and an intended compound can be obtained by proper choice of base, with an unexpectedly high selectivity being attained.

The reaction solvents are not critically limited so far as they are free of active proton. Preferably, solvents having high solubility are employed from the standpoint of productivity. Examples of such solvents include dimethylformamide (DMF), dimethylacetamide (DMAc), N,N-dimethylimidazoline-2-on (DMI), acetonitrile, tetrahydrofuran, chloroform, methylene chloride and the like. The reaction temperature is preferably in the range of from 0° to 80° C. and most preferably from 5° to 50° C. in order to ensure high selectivity.

[Step 2]

In order to obtain benzoxazole derivative [I] by ring-closure reaction of compound [IV], the dehydration reaction is effected in the presence of an acid catalyst. The acid catalysts may be all organic and inorganic acids which are ordinarily used in the field of organic synthesis. Preferable examples include organic sulfonic acids such as p-toluenesulfonic acid, methanesulfonic acid and the like, organic carboxylic acids such as formic acid, trichloracetic acid, benzoic acid and the like, inorganic acids such as sulfuric acid, phosphoric acid, polyphosphoric acid, sulfur pentaoxide, acid clay and the like, and Lewis acids such as zinc chloride, aluminum chloride, titanium chloride and the like. Suitable solvents for the reaction include those which make azeotrope with water, e.g., aromatic solvents such as xylene, toluene, benzene, anisole and the like, chlorinated solvents such as tetrachloroethane, dichloroethane, methyl chloroform, chloroform and the like, and ether solvents such as diethoxyethane, diglime, dimethoxyethane and the like. For increasing the solubility, co-solvents may be added including, for example, DMF, DMAc, methyl cellosolve acetate, DMI, diethylene glycol and the like.

In view of the organic synthetic chemistry, it is the common practice that benzoxazole derivatives are obtained by the dehydration and ring closure reaction of o-amidophenol as particularly described in U.S. Pat. No. 3,880,661 and Japanese Patent Application (OPI) No. 153923/77 etc. However, in the synthesis of compound [I], the conversion of a compound of the following general formula [VI], which is an isomer of compound [IV], into compound [I] is disadvantageous in that the reaction is very slow and requires high temperature with a low reaction yield.

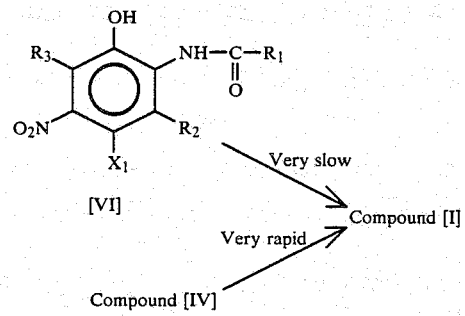

In contrast, the dehydration and ring closure reaction in the step (2) proceeds very rapidly. According to this step (2), the reaction completes in high yield at low temperatures within a short period without coloration of the reaction solution and the amount of an acid catalyst used can be reduced. These are unexpected results.

The compound [I], which is a key compound in the process of the invention, may be prepared by a process which is slightly different from the process including the above steps (1) and (2). For instance, 4-chloro- (or bromo-)2-aminophenol derivatives are converted to benzoxazole derivatives according to the process described in U.S. Pat. No. 3,880,661, followed by nitration. However, this process is inferior to the process using the steps (1) and (2) for the reason that the yield on nitration is low. Further the process using steps (1) and (2) is superior in that 2-amino-4-chloro (or bromo-)5-nitrophenol derivatives of the general formula [V] is industrially and inexpensively available.

[Step 3]

Preparation of the compound of the general formula [III] from the compound of the general formula [I] is achieved by substitution reaction between $X_2$ and $X_1$. In this reaction, where oxygen atom is substituted, it is favorable to generate oxygen atom anion and then react the anion with compound [I]. This is also applied to the case of a methyl group substituted with sulfur atom and an electron attractive group. When nitrogen atom is used for $X_2$ substitution, it is preferable to use, for reaction with compound [I], $X_2H$ where a highly basic nitrogen atom is used, or $X_2^\ominus$ where there is used a nitrogen atom whose basicity is low. The substitution reaction may be effected in the presence of metals or metal ions such as $Cu$, $Cu^+$, $Cu^{2+}$ and the like as is known as the Ullmann reaction. The molar ratio compound [I] and a nucleophilic agent, $X_2H$, is not critical and is generally 1:1. One of them, whichever more inexpensive, may be used in excess.

The reaction solvents may be any solvents which are aprotic and are not dissociated or decomposed under alkaline conditions. Preferably, there are used aromatic solvents such as xylene, toluene, anisole, nitrobenzene, benzene and the like, ether solvents such as diglime, dimethoxyethane, dioxane, tetrahydrofuran and the like, amide solvents such as DMAc, DMF, DMI, hexamethylphosphoric amide, N-methylpyrrolidone and the like, and halogenated solvents such as dichloroethane, chloroform and the like. The reaction temperature may vary depending on the degree of nucleophilicity of $X_2$, and is generally in the range of from $-40°$ C. to $180°$ C., preferably from $0°$ C. to $140°$ C.

[Step 4]

The opening of the benzoxazole ring by hydrolysis is usually under acidic conditions, by which an amino product is obtained through an amide compound (see, for example, the afore-indicated U.S. Pat. No. 3,880,661, and Japanese Patent Application (OPI) Nos. 153923/77, 153775/80 and 100771/81).

The ring opening is considered to start from addition of proton to the C=N bond of the benzoxazole ring. The resulting aminophenol product or amidophenol product is kept stable under acidic conditions, so that this process is usually used as a technique of opening benzoxazole or oxazole ring. When compound [III] is subjected to ring-opening the reaction according to methods as described in the afore-indicated Japanese Patent Application (OPI) Nos. 153923/77 and 153775/80, or in the presence of other acids such as, for example, diluted sulfuric acid, bromine water, iodine water, methanesulfonic acid, p-toluenesulfonic acid, formic acid, acetic acid and the like, compounds of the general formula [II] in which $R_4=COR_1$ are obtained. However, when the reaction is caused to further proceed until the amido is hydrolyzed, the reaction solution turns into a black tar, so that no aminophenol derivatives of the formula where $R_4=H$ cannot be obtained as crystals. This requires an additional isolation operation using column chromatography. Even here, by-products are contained in large amounts and the yield is at most as small as 10 to 30%.

In such a case, when the reaction is carried out under alkaline conditions, e.g. aqueous NaOH solution, aqueous KOH solution, or $CH_3ONa$, which is exceptional for the ring-opening of benzoxazole, there is quickly obtained a compound of the formula [II] where $R_4=H$ through $R_4=COR_1$. To a surprise, the yield becomes almost quantitative. Thus, with compound [III], the ring-opening reaction in alkaline conditions are favorable, under which the resulting aminophenol product of the formula [II] where $R_4=H$ is kept more stable. The solvents suitable for hydrolysis are water and aqueous solutions of water-miscible solvents. The water-miscible co-solvents are preferably various alcohols (e.g., methanol, ethanol, isopropanol, butanol, methyl cellosolve), and ethers (e.g., diethyl ether, tetrahydrofuran, dioxane, diglime). In order to increase the solubility, co-solvents may be used including, for example, DMSO, SMF, DMAc DMI, HMPA, acetonitrile and the like. Alternatively, solvents which are immiscible with water (e.g., toluene, benzene, dichloroethane) may be added to form a two phase system. In this case, a phase transfer catalysis, e.g. quaternary ammonium salts, may be used.

The hydrolysis of the step (3) is preferably performed at a reaction temperature of from 50° to 150° C. under alkaline conditions, and at a temperature of from 50° to 150° C. under acidic conditions.

The reason why compound [IV] is selectively obtained in step (1) is not known, but it is considered due to the fact that the amino group of compound [V] lowers in reactivity because the compound has the nitro group at the para position and $X_2$ (chlorine or bromine atom) at the meta position with respect to the amino group. However, taking the high selectivity into account, factors other than the lowering of the reactivity are assumed to contribute to the selective formation.

In the step (2), the dehydration and ring closure reaction proceeds very rapidly, so that the reaction is completed rapidly at relatively low temperatures with a reduced degree of coloration of the reaction solution. The reaction yield is high and the amount of an acid catalyst used can be reduced. These advantages are considered to result from the specific action of compound [IV].

In the step (3), when fluoro compound [VII] is replaced by chloro compound [IX], no appreciable reaction, as expected, takes place, but only compounds of unknown structures are produced. In contrast, when using compound [I] of the invention, substituted compound [III] is obtained in high yield similar to the case of fluoro compound [VII]. Presumably, this means that the chlorine or bromine atom in compound [I] has the same reactivity as the fluorine atom in compound [VII]. This is considered to be rather an abnormal phenomenon. With compound [IX] having a methyl group, the expected compound [X] is scarcely obtained, but products of unknown structures are given. From this, it is believed that the benzoxazole ring in compound [I] is stabilized. However, higher stabilization should be more disadvantageous for substitution reaction. In this sense, the reason why compound [I] is highly reactive cannot be explained by any known theories.

(Specific Examples of Compounds of the Invention)

Compounds to which the process of the present invention is applied are exemplified only by way of explanation.

TABLE 1

| Compound No. | $R_1$ | $R_2$ | $R_3$ | $X_1$ |
|---|---|---|---|---|
| [I]-(1), [IV]-(1) | 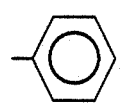 | H | H | Cl |
| [I]-(2), [IV]-(2) | 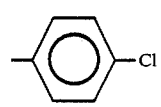 | H | H | Cl |

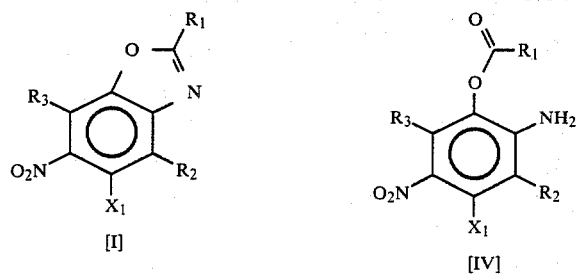

TABLE 1-continued

Structure [I]: benzene ring with O-C(=O)-R₁ at position 1, N= at position 2, R₂ at position 3, X₁ at position 4, NO₂ at position 5, R₃ at position 6.

Structure [IV]: benzene ring with O-C(=O)-R₁ at position 1, NH₂ at position 2, R₂ at position 3, X₁ at position 4, NO₂ at position 5, R₃ at position 6.

| Compound No. | R₁ | R₂ | R₃ | X₁ |
|---|---|---|---|---|
| [I]-(3), [IV]-(3) | 2-chlorophenyl | H | H | Cl |
| [I]-(4), [IV]-(4) | 2,4-dichlorophenyl | H | H | Cl |
| [I]-(5), [IV]-(5) | 2-methylphenyl | H | H | Cl |
| [I]-(6), [IV]-(6) | 4-tert-butylphenyl (—C₄H₉(t)) | H | H | Cl |
| [I]-(7), [IV]-(7) | 2-methoxyphenyl (—OCH₃) | H | H | Cl |
| [I]-(8), [IV]-(8) | 4-dodecyloxyphenyl (—OC₁₂H₂₅) | H | H | Cl |
| [I]-(9), [IV]-(9) | 2-naphthyl | Cl | Cl | Cl |
| [I]-(10), [IV]-(10) | pentafluorophenyl (F,F,F,F,F) | H | H | Cl |
| [I]-(11), [IV]-(11) | —C(CH₃)₃ (tert-butyl) | H | H | Cl |

TABLE 1-continued

[Structures shown:
[I]: benzoxazole with R1 on C=N-O, R3, O2N, X1, R2 substituents on benzene ring
[IV]: phenyl ester with O-C(=O)-R1, NH2, R3, O2N, X1, R2 substituents]

| Compound No. | R₁ | R₂ | R₃ | X₁ |
|---|---|---|---|---|
| [I]-(12), [IV]-(12) | -C(CH₃)₂-C₉H₁₉ | H | H | Cl |
| [I]-(13), [IV]-(13) | -C₃F₇ | H | H | Cl |
| [I]-(14), [IV]-(14) | 2-furyl | H | H | Cl |
| [I]-(15), [IV]-(15) | 3-pyridyl | H | H | Cl |
| [I]-(16), [IV]-(16) | -CH(C₂H₅)C₄H₉ | H | H | Cl |
| [I]-(17), [IV]-(17) | cyclohexyl | H | CH₃O— | Cl |
| [I]-(18), [IV]-(18) | -CH(CH₃)₂ | H | H | Cl |
| [I]-(19), [IV]-(19) | -CH(C₂H₅)-O-(2-C₅H₁₁(t), 4-CH₃-phenyl) | CH₃— | Cl | Cl |
| [I]-(20), [IV]-(20) | -C(CH₃)=CH₂ | H | H | Cl |
| [I]-(21), [IV]-(21) | -CH=CH-C₆H₅ | H | H | Cl |
| [I]-(22), [IV]-(22) | -CH=CH-OCH₃ | H | H | Cl |
| [I]-(23), [IV]-(23) | -C≡CH | CH₃ | CH₃ | Cl |
| [I]-(24), [IV]-(24) | -C≡C-CH₃ | H | Cl | Cl |
| [I]-(25), [IV]-(25) | -CH(OCH₃)-C₆H₁₃ | H | CH₃O | Cl |
| [I]-(26), [IV]-(26) | -C(=O)H | H | H | Cl |

TABLE 1-continued

Structures [I] and [IV] as shown.

| Compound No. | R₁ | R₂ | R₃ | X₁ |
|---|---|---|---|---|
| [I]-(27), [IV]-(27) | —C(=O)—C₆H₅ (benzoyl) | H | H | Cl |
| [I]-(28), [IV]-(28) | —N(CH₃)₂ | H | H | Cl |
| [I]-(29), [IV]-(29) | morpholino | H | H | Cl |
| [I]-(30), [IV]-(30) | 4-methylpiperazin-1-yl | H | H | Cl |
| [I]-(31), [IV]-(31) | imidazolin-1-yl | H | H | Cl |
| [I]-(32), [IV]-(32) | —N(CH₃)—C(=O)—C₆H₅ | H | Cl | Cl |
| [I]-(33), [IV]-(33) | C₆H₅ | H | Cl | Cl |
| [I]-(34), [IV]-(34) | C₆H₅ | H | H | Br |
| [I]-(35), [IV]-(35) | 4-OCH₃—C₆H₄ | H | H | Br |
| [I]-(36), [IV]-(36) | 2,4-di-Cl—C₆H₃ | H | Br | Br |
| [I]-(37), [IV]-(37) | —C(CH₃)₃ | H | H | Br |

TABLE 1-continued
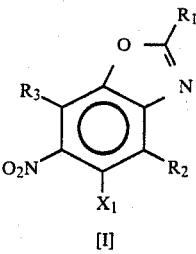
[I]
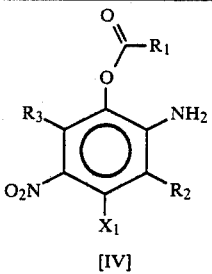
[IV]
| Compound No. | R₁ | R₂ | R₃ | X₁ |
|---|---|---|---|---|
| [I]-(38), [IV]-(38) | 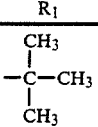 | H | Br | Br |
| [I]-(39), [IV]-(39) |  | CH₃O— | H | Br |
| [I]-(40), [IV]-(40) |  | H | Br | Br |
| [I]-(41), [IV]-(41) | 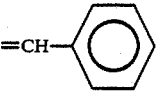 | H | H | Br |
| [I]-(42), [IV]-(42) | 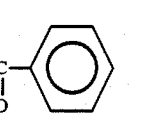 | H | H | Br |
| [I]-(43), [IV]-(43) | 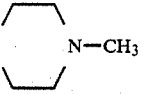 | H | CH₃— | Br |
| [I]-(44), [IV]-(44) | 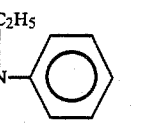 | H | H | Br |
| [I]-(45), [IV]-(45) | 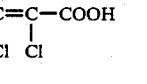 | H | H | Br |
| [I]-(46), [IV]-(46) | 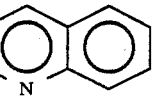 | H | H | Cl |
| [I]-(47), [IV]-(47) | 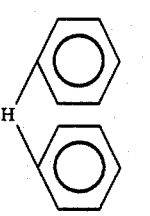 | H | H | Cl |
| [I]-(48) | 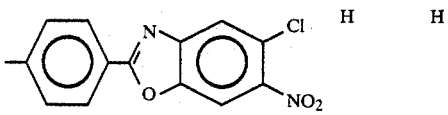 | H | H | Cl |

TABLE 1-continued

| Compound No. | R₁ | R₂ | R₃ | X₁ |
|---|---|---|---|---|
| [I]-(49) | 5-chloro-6-nitro-2-benzoxazolyl (methyl-substituted) | H | H | Cl |
| [I]-(50) | —CH=CH—(5-chloro-6-nitro-2-benzoxazolyl) | H | H | Cl |

TABLE 2

[Structure III: benzoxazole with R1-C(=N)-O fused to benzene ring bearing R2, R3, X2, and O2N substituents]

| Compound No. | R1 | R2 | R3 | X2 |
|---|---|---|---|---|
| [III]-(1) | phenyl | H | H | phenoxy |
| [III]-(2) | phenyl | H | H | 2,5-dichlorophenoxy (Cl at 2 and 5) |
| [III]-(3) | phenyl | H | H | 4-(t-C8H17)phenoxy |
| [III]-(4) | 2-naphthyl | H | H | 4-methoxyphenoxy |
| [III]-(5) | phenyl | H | H | 3-methoxyphenoxy |
| [III]-(6) | phenyl | H | H | 2-methoxyphenoxy |

TABLE 2-continued
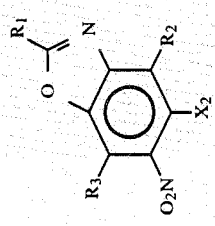
[III]
| Compound No. | R₁ | R₂ | R₃ | X₂ |
|---|---|---|---|---|
| [III]-(7) |  2,4-Cl₂-C₆H₃ | H | H | 4-OCH₃-C₆H₄-O- |
| [III]-(8) |  C₆H₅ | H | H | 4-OH-C₆H₄-O- |
| [III]-(9) |  C₆H₅ | H | H | 4-OC₄H₉-C₆H₄-O- |
| [III]-(10) |  C₆H₅ | H | H | 4-OCH₂CH₂OCH₃-C₆H₄-O- |
| [III]-(11) |  C₆H₅ | H | H | 4-C₄H₉(t)-C₆H₄-O- |
| [III]-(12) | 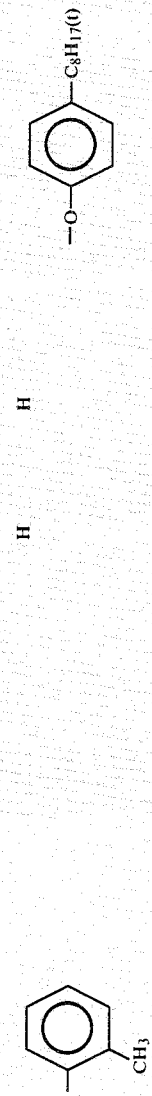 2-CH₃-C₆H₄ | H | H | 4-C₈H₁₇(t)-C₆H₄-O- |

TABLE 2-continued

[III]

| Compound No. | $R_1$ | $R_2$ | $R_3$ | $X_2$ |
|---|---|---|---|---|
| [III]-(13) | 4-Cl-C6H4 | H | H | 4-C8H17(t)-C6H4-O- |
| [III]-(14) | C6H5 | H | H | 4-C5H11(t)-C6H4-O- |
| [III]-(15) | C6H5 | H | H | 3-C5H11(t)-4-C5H11(t)-C6H3-O- |
| [III]-(16) | C6F5 | H | H | 4-C8H17(t)-C6H4-O- |
| [III]-(17) | 3,5-Cl2-C6H3 | H | H | 4-C8H17(t)-C6H4-O- |

TABLE 2-continued

[III structure: R1-C(=N)-O on benzene ring with R2, R3, X2, O2N substituents]

| Compound No. | R1 | R2 | R3 | X2 |
|---|---|---|---|---|
| [III]-(18) | phenyl | H | H | 3-pentadecyl-phenoxy (C15H31) |
| [III]-(19) | —C4H9(t) | H | H | 4-methoxyphenoxy (OCH3) |
| [III]-(20) | —C4H9(t) | H | H | 4-(n-octyl)phenoxy (C8H17(n)) |
| [III]-(21) | —C4H9(t) | H | H | 2-methoxy-5-acetamidophenoxy (NHCOCH3, OCH3) |
| [III]-(22) | —C(CH3)2—C9H19 | H | Cl | 4-(4-benzyloxyphenylsulfonyl)phenoxy (SO2-C6H4-OCH2-C6H5) |
| [III]-(23) | —C8F16H | H | H | 4-(n-octyl)phenoxy (C8H17(n)) |

TABLE 2-continued

[III]

(structure: benzene ring with R1-C(=N)-O- at one position, R2, R3, X2, O2N substituents)

| Compound No. | R1 | R2 | R3 | X2 |
|---|---|---|---|---|
| [III]-(24) | —C3F7 | H | H | -O-C6H4-OCH3 (para) |
| [III]-(25) | 2-methylfuran-5-yl | H | H | -O-C6H4-C8H17(t) (para) |
| [III]-(26) | —CH(C2H5)—C4H9 | H | H | -O-C6H4-C8H17(t) (para) |
| [III]-(27) | cyclohexyl | H | H | -O-C6H4-COOC2H5 (para) |
| [III]-(28) | —CH=CH—C6H5 | H | H | -O-C6H4-C8H17(t) (para) |
| [III]-(29) | —CH(CH3)—CH3 | H | H | —S—CH(COOC2H5)C12H25 |
| [III]-(30) | —CH(C4H9)—C2H5 | H | H | —S—C6H4—C12H25 (para) |

TABLE 2-continued

| Compound No. | R₁ | R₂ | R₃ | X₂ |
|---|---|---|---|---|
| [III]-(31) | phenyl | H | H | N-morpholino |
| [III]-(32) | 4-OC₈H₁₇-phenyl | H | H | N-pyrrolidino |
| [III]-(33) | phenyl | H | H | 4-(C₁₂H₂₅SO₂)-phenyl |
| [III]-(34) | phenyl | H | H | 4-CH₃O-phenyl-SCH₃ |
| [III]-(35) | phenyl | H | H | 4-CH₃O-phenyl-SO₂CH₃ |

TABLE 2-continued

[III structure: R1-C(=O)-O-benzene ring with R2, R3, X2, O2N substituents]

| Compound No. | R1 | R2 | R3 | X2 |
|---|---|---|---|---|
| [III]-(36) | phenyl | H | H | 2-phenyl-1,3,4-thiadiazol-5-ylthio |
| [III]-(37) | phenyl | H | CH3O— | —N(CH2CH2OCH3)2 |
| [III]-(38) | pentafluorophenyl | H | H | —F |
| [III]-(39) | phenyl | H | H | —OCH2COCH3 |
| [III]-(40) | phenyl | H | H | —S-(2-OC4H9, 5-C8H17(t))phenyl |

TABLE 2-continued

Structure [III]:

A phenyl ring with substituents: $R_1C(=N)O-$ at one position, $R_2$, $R_3$, $NO_2$, and $X_2$ on the ring.

| Compound No. | $R_1$ | $R_2$ | $R_3$ | $X_2$ |
|---|---|---|---|---|
| [III]-(41) | phenyl | H | H | $-C\equiv N$ |
| [III]-(42) | $-C_4H_9(t)$ | H | H | benzotriazol-1-yl with 5-COOCH$_3$ |
| [III]-(43) | $-C_4H_9(t)$ | H | H | $-S-C\equiv N$ |
| [III]-(44) | $-C_4H_9(t)$ | H | H | 4-OC$_4$H$_9$, 2-S-(4-C$_8$H$_{17}$(t)-phenyl) |
| [III]-(45) | $-C_4H_9(t)$ | H | H | $-O-N(CH_3)-C(=O)-C_6H_5$ |
| [III]-(46) | $-C_4H_9(t)$ | H | H | $-N_3$ |
| [III]-(47) | $-C_4H_9(t)$ | H | H | $-F$ |
| [III]-(48) | $-C_4H_9(t)$ | H | Cl | $-CH(COCH_3)_2$ |
| [III]-(49) | $-C_4H_9(t)$ | H | H | $-C\equiv N$ |
| [III]-(50) | $-C_4H_9(t)$ | H | H | $-O-C(=O)-C_3H_7$ |

TABLE 2-continued

[III]

[Structure: benzoxazole-type ring with R1 on C=N/O carbon, R2, R3 on benzene ring, O2N and X2 substituents]

| Compound No. | R1 | R2 | R3 | X2 |
|---|---|---|---|---|
| [III]-(51) | −C(CH₃)₂CH₃ (−C(CH₃)₂−C₉H₁₉, with two CH₃ groups) | H | F | −SO₃Na |
| [III]-(52) | −C₈F₁₆H | H | H | −NHS(=O)₂−CH₃ |
| [III]-(53) | 2-furyl | CH₃O− | H | −S−S(=O)₂−ONa |
| [III]-(54) | 2-pyridyl | CH₃ | CH₃ | −C≡N |
| [III]-(55) | cyclohexyl | H | CH₃O | −NHCON(CH₃)(C₆H₅) |
| [III]-(56) | −C₄H₉(t) | H | H | −S−C(=NH)NH₂ · HCl |
| [III]-(57) | −C₄H₉(t) | H | H | −SCH₂CH₂N(CH₃)₂ |

TABLE 2-continued

| Compound No. | R₁ | R₂ | R₃ | X₂ |
|---|---|---|---|---|
| [III]-(58) | 2-(4-methylphenyl)benzoxazol-5-yl-oxy-6-nitrophenyl | H | H | 4-methoxyphenoxy |
| [III]-(59) | 2-methylbenzoxazol-5-yl-(4-t-octylphenoxy)-nitro | H | H | 4-t-octylphenoxy |
| [III]-(60) | –CH=CH– with O(CH₂)₃CO₂CH₃ and NO₂ substituents | H | H | –O(CH₂)₃CO₂CH₃ |
| [III]-(61) | N-methyl-N-phenylamino | H | Cl | cyanuric acid residue |
| [III]-(62) | morpholino | H | H | 1-phenyl-2-oxopyrrolidin-3-yl |

TABLE 2-continued

| Compound No. | R₁ | R₂ | R₃ | X₂ |
|---|---|---|---|---|
| [III]-(63) | 2-methylquinolin-8-yl | H | H | −O−C₆H₄−OH (para) |
| [III]-(64) | −N(C₈H₁₇)₂ | H | H | −OCH₂CONHCH₃ |
| [III]-(65) | −NCH₂CH₂OCH₃ <br> \|<br>CH₃ | H | H | −N-(2-oxopyrrolidin-1-yl) |

TABLE 3
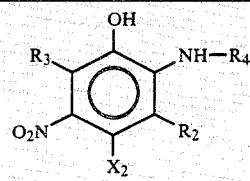
[II]
| Compound | $X_2$ | $R_2$ | $R_3$ | $R_4$ |
|---|---|---|---|---|
| [II]-(1) | —O—C₆H₅ | H | H | H |
| [II]-(2) | —O—C₆H₄—F | H | H | H |
| [II]-(3) | —O—C₆H₄—Cl | H | H | H |
| [II]-(4) | —O—C₆H₄—Cl | H | H | —COC₃F₇ |
| [II]-(5) | —O—C₆H₄—CO₂H | H | H | H |
| [II]-(6) | —O—C₆H₄—OCH₃ | H | H | H |
| [II]-(7) | —O—C₆H₄—C₈H₁₇(t) | H | H | H |
| [II]-(8) | —O—C₆H₄—C₈H₁₇(t) | H | H | —CO—C₆H₅ |
| [II]-(9) | —O—C₆H₄—SO₂CH₃ | H | H | H |
| [II]-(10) | —O—C₆H₄—OCH₃ (meta) | H | H | H |
| [II]-(11) | —O—C₆H₄(NHSO₂CH₃) | H | H | H |

TABLE 3-continued

[II]

Structure: Phenol with OH, R3 (position 6), NH-R4 (position 2), O2N (position 5), R2 (position 3), X2 (position 4)

| Compound | X2 | R2 | R3 | R4 |
|---|---|---|---|---|
| [II]-(12) | —O—(C6H4)—OCH3 (para) | H | H | —COC3F7 |
| [II]-(13) | —O—(C6H4)—OC4H9 (para) | H | H | H |
| [II]-(14) | —O—(C6H4)—C8H17(t) (para) | H | H | —CO-(2-furyl) |
| [II]-(15) | —O—(C6H4)—NO2 (para) | H | H | —CO-(2-furyl) |
| [II]-(16) | —S—(C6H4)—C12H25 (para) | H | H | H |
| [II]-(17) | —SO2—(C6H4)—C12H25 (para) | H | H | H |
| [II]-(18) | —S—C16H33 | H | H | H |
| [II]-(19) | —S—(C6H3)(OC4H9)(C8H17(t)) | H | H | —CO—C6H5 |
| [II]-(20) | —SCH(C12H25)CO2C2H5 | H | H | H |
| [II]-(21) | —SO2CH3 | H | H | —COC4H9(t) |
| [II]-(22) | —N(pyrazolyl) | H | H | H |
| [II]-(23) | —N(pyrazolyl) | H | Cl | H |
| [II]-(24) | —N(morpholino) | H | H | H |
| [II]-(25) | —N(C8H17)2 | H | Cl | H |

TABLE 3-continued

Structure [II]:

$$\text{2,4-disubstituted phenol with } R_3, OH, NH-R_4, R_2, X_2, O_2N \text{ substituents}$$

| Compound | $X_2$ | $R_2$ | $R_3$ | $R_4$ |
|---|---|---|---|---|
| [II]-(26) | —OH | H | Br | —CO—C₆H₅ (phenyl) |
| [II]-(27) | —OCH₃ | H | H | H |
| [II]-(28) | —F | H | H | —CO—C₆F₄ (pentafluorobenzoyl) |
| [II]-(29) | —O(CH₂)₂SO₂CH₃ | H | H | H |
| [II]-(30) | —OCH₂—C₆H₅ | H | H | H |
| [II]-(31) | —O—(2,4-dichlorophenyl) | H | H | H |
| [II]-(32) | —O—biphenyl | H | H | H |
| [II]-(33) | —O—C₆H₄—CH₃ | H | H | H |
| [II]-(34) | —O—C₆H₄—C₁₅H₃₁ | H | H | H |
| [II]-(35) | —O—C₆H₄—NHCOC₁₅H₃₁ | H | H | H |
| [II]-(36) | —O—C₆H₄—OCH₂COOH | H | H | H |
| [II]-(37) | —O—C₆H₄—O(CH₂)₃COOH | H | H | H |

TABLE 3-continued

Structure [II]: phenol with OH, R3, NH—R4, O2N, X2, R2 substituents

| Compound | X2 | R2 | R3 | R4 |
|---|---|---|---|---|
| [II]-(38) | —O—C6H4—CH2O—C6H5 | H | H | H |
| [II]-(39) | —O—C6H4—OC8H17 | H | H | H |
| [II]-(40) | —O—C6H4—OCH3 | Cl | Cl | H |
| [II]-(41) | —O—C6H4—OCH3 | H | Cl | —CO—C4H9(t) |
| [II]-(42) | —O—C6H4—OCH3 | H | Br | —CO—(2-pyridyl) |
| [II]-(43) | —CH(SO2CH3) | H | H | H |
| [II]-(44) | —CH(CO2H)2 | H | Cl | H |
| [II]-(45) | —C(O)NH2 | CH3O— | H | H |
| [II]-(46) | —NHSO2CH3 | H | Cl | H |
| [II]-(47) | —NHCO—C6H5 | Cl | H | —C(O)—N(CH3)(C6H5) |
| [II]-(48) | —SO3Na | H | H | H |
| [II]-(49) | —OCH2CONHCH3 | H | H | H |
| [II]-(50) | —O—C6H4—OH | H | H | —CO—(2-Cl-C6H4) |

Features and advantages of the present invention are summarized below.

(1) 2-Amino-5-nitrophenol derivatives into which various nucleophilic groups are introduced at the 4 position can be prepared using starting materials which are inexpensive and readily available.

(2) No treatment of waste water containing fluorine ions is necessary as is essential in the prior art. Accordingly, conventional equipments are used to prepare the derivatives safely.

(3) The derivatives can be prepared in high yield by a simple procedure.

(4) The derivatives can be prepared at low product cost.

To further illustrate this invention, and not by way of limitation, the following examples are given.

SYNTHESIS EXAMPLE 1

(Synthesis of Exemplified Compound [IV]-(1))

377 g (2 moles) of 2-amino-4-chloro-5-nitrophenol and 280 ml (2 moles) of triethylamine were added to 1 liter of N,N-dimethylacetoamide, followed by dropping 281 g (2 moles) of benzoyl chloride at about 50° C. in about 30 minutes. After continuing the agitation for further 30 minutes, 1 liter of methanol and 1 liter of water were added to the reaction solution. The resulting crystals were filtered and washed with 1 liter of methanol, thereby obtaining 547 g (yield 94%) of exemplified compound [IV]-(1).

m.p. 207°-210° C., IR spectrum $\nu C=O$, 1725 cm$^{-1}$.

<Another Way of Synthesis of Exemplified Compound [IV]-(1)>

188 g (1 mole) of 2-amino-4-chloro-5-nitrophenol and 122 g (1 mole) of 4-dimethylaminopyridine were added to 2 liters of acetonitrile, into which 140 g (1 mole) of benzoyl chloride was dropped at room temperature in about 30 minutes. While the temperature of the reaction solution rose up to 50° C., the agitation was continued for 30 minutes. 200 ml of water was added to the reaction solution and the resulting crystals were filtered, followed by washing with 400 ml of 50% methanol, thereby obtaining 245 g of [IV]-(1) in a yield of 84%. m.p. 208°-210° C.

According to the above procedure, there were prepared various compounds [IV]. The melting points of typical compounds is shown below.

| Compounds | m.p. |
|---|---|
| [IV]-(1) | 208–210° C. |
| [IV]-(4) | 189–191° C. |
| [IV]-(6) | 185–188° C. |
| [IV]-(8) | 113–115° C. |
| [IV]-(11) | 135–137° C. |
| [IV]0(14) | 202–205° C. |
| [IV]-(16) | oil |
| [IV]-(18) | 105–108° C. |
| [IV]-(21) | 184–186° C. |
| [IV]-(37) | 120–122° C. |

REFERENCE EXAMPLE 1

188 (1 mole) g of 2-amino-4-chloro-5-nitrophenol and 79 g (1 mole) of pyridine were added to 500 ml of N-dimethylacetamide, followed by dropping 140 g (1 mole) of benzoyl chloride at about 5° C. in about 30 minutes and agitating for further 30 minutes. The resulting crystals were filtered and washed with 500 ml of methanol to obtain 260 g (yield 89%) of an isomer of exemplified compound [IV]-(1) (2-benzamido-4-chloro-5-nitrophenol). From the melting point of below 250° C. and an IR spectrum ($\nu C=O$, 1654 cm$^{-1}$), this compound was found to be 2-benzamide compound.

As will be clear from the results of Reference Example 1, the reaction is affected in the presence of a base such as pyridine having a pka value below 6, the N-acyl product is obtained as a main product (rate of formation; over 90%), but an intended ester product cannot be obtained. As particularly described in Synthetic Example 1, o-acyl products are selectively obtained only in the presence of a strong base such as triethylamine (pka value of 7–12, preferably 10–12).

SYNTHESIS EXAMPLE 2

(Synthesis of Exemplified Compound [I]-(1))

293 g (1 mole) of exemplified compound [IV]-(1) and 76 g (0.4 mole) of p-toluenesulfonic acid monohydrate were added to 3 liters of toluene and heated under reflux. The heating under reflux was continued for 1 hour while removing azeotropic water using a water separator. As a result, about 23 ml of water was distilled off. The reaction solution as filtered as heated and then cooled, as it is, at room temperature, followed by further cooling with ice water down to about 10° C., after which the resulting crystals were filtered. The crystals were washed with 2 liters of methanol until the pH of the filtrate was 6–7, thereby obtaining 250 g (yield 91%) of exemplified compound [I]-(1). m.p. 199°-201° C.

REFERENCE EXAMPLE 2

The 2-benzamido-4-chloro-5-nitrophenol compound obtained in Reference Example 1 was used to compare with the compound [IV]-(1) of the invention obtained in Synthetic Example 2 with regard to ring closure reaction.

293 g (1 mole) of 2-benzamido-4-chloro-5-nitrophenol and 76 g (0.4 mole) of p-toluenesulfonic acid monohydrate were added to 3 liters of toluene, followed by heating under reflux. With [IV]-(1), 1 hour after the reaction had been almost completed, the crystals precipitated from the reaction solution were tested to confirm its structure. It was found that the crystals were those of the starting material. Further, the reaction was continued and, 5 hours after heating under reflux, part of the reaction solution was sampled to confirm the structure, with the result that about 40% of a ring-closed product was formed with the balance of the starting material and by-products. The reaction was further continued and after 20 hours, the ring-closed product reached about 70%, but colored components ascribed to the high temperature and long time reaction increased in amounts, thus lowering the quality of the product.

As will be apparent from the results of Reference Example 2 and Synthetic Example 2, the ester product [IV]-(1) is found to be better than the amido product in reduction of the reaction time, yield and quality.

SYNTHESIS EXAMPLE 3

(Synthesis of Exemplified Compound [I]-(11))

273 g (1 mole) of exemplified compound [IV]-(11) and 9.5 (0.05 mole) of p-toluenesulfonic acid monohydrate were added to a mixed solvent of 0.5 liters of toluene and 0.2 liters of diglime and heated under reflux for about 2 hours. During the heating, azeotropic water was removed by the use of a water separator and about 24 ml of water was distilled off. When the azeotropy of water terminated, the solvent was completely distilled off under reduced pressure. The resulting oil product was washed with water and remaining p-toluenesulfonic acid was removed, after which 300 ml of n-hexane was added and the resulting crystals were collected by filtration, thereby obtaining 242 g (yield 95%) of exemplified compound [I]-(1). m.p. 79°-81° C.

The compounds of general formula [I] could be obtained according to the procedure described in Synthetic Examples 2 and 3. The melting points of typical compounds are shown in Table 4 below.

TABLE 4

| Compound No. | m.p. (°C.) | Compound No. | m.p. (°C.) |
|---|---|---|---|
| [I]-(1) | 199–201 | [I]-(11) | 79–81 |
| [I]-(2) | 188–189 | [I]-(14) | 250< |
| [I]-(3) | 172–173 | [I]-(16) | Oil |
| [I]-(4) | 179–181 | [I]-(18) | 80–81 |
| [I]-(5) | 196–197 | [I]-(21) | 186–187 |
| [I]-(6) | 166–168 | [I]-(34) | 181–184 |

TABLE 4-continued

| Compound No. | m.p. (°C.) | Compound No. | m.p. (°C.) |
| --- | --- | --- | --- |
| [I]-(8) | 91-92 | [I]-(37) | 75-77 |

SYNTHESIS EXAMPLE 4

(Synthesis of Exemplified Compound [III]-(3))

20.6 g (0.1 mole) of 4-t-octylphenol and 3.9 g (0.1 mole) of potassium hydroxide were added to 150 ml of toluene and heated under reflux for 2 hours, during which azeotropic water was removed using a water separator, thereby obtaining 4-t-octylphenoxy potassium. To this suspension were added a solution of 31.9 g (0.1 mole) of exemplified compound [I]-(34) in 100 ml of DMF and 0.5 g of cuprous chloride, followed by agitating under heating conditions in a stream of nitrogen at about 80° C. for 2 hours. The reaction solution was cooled, to which 200 ml of methanol was added. The resulting crystals were collected by filtration to obtain 36.9 g (yield 83%) of exemplified compound [III]-(3). m.p. 183°–185° C.

SYNTHESIS EXAMPLE 5

(Synthesis of Exemplified Compound [III]-(7))

124 g (1 mole) of 4-hydroxyanisole and 38.8 g (1 mole) of potassium hydroxide were added to 1.4 liters of toluene and heated under reflux for 3 hours. During the heating, azeotropic water was removed by the use of a water separator to obtain a potassium salt of 4-hydroxyanisole. To the reaction solution were added a 700 ml of DMF solution of 342 g (1 mole) of [I]-(4) and 4 g of copper powder, followed by heating at about 85° C. for 3.5 hours. The hot reaction solution was filtered to remove the copper powder, to which 1.5 liters of methanol was added. The solution was cooled down to about 10° C. The resulting crystals were collected by filtration to obtain 347 g (yield 87%) of exemplified compound [III]-(7) in the form of yellowish brown crystals. m.p. 144°–146° C.

SYNTHESIS EXAMPLE 6

(Synthesis of Exemplified Compound [III]-(20))

To a solution of 206 g (1 mole) of 4-t-octylphenol in 1 liter of toluene was added 24 g (1 mole) of sodium hydride, followed by continuing agitation for 1 hour to obtain a sodium salt of 4-t-octylphenol. Subsequently, a solution, in 1 liter of tetrahydrofuran, of 255 g (1 mole) of [I]-(11) obtained in Synthetic Example 3 was added to the reaction solution, followed by heating under reflux for 2 hours. After cooling the reaction solution, about 1 liter of the solvent was distilled off by means of an evaporator, to which 500 ml of water and 500 ml of ethyl acetate for phase separation. The organic phase was dried using Glauber's salt, from which the solvent was removed to obtain an oily substance. One liter of hexane was added to the oily substance and agitated, and the resulting crystals were collected by filtration to obtain 419 g (yield 95%) of exemplified compound [III]-(20) in the form of light brown crystals. m.p. 77°–78° C.

SYNTHESIS EXAMPLE 7

(Synthesis of Exemplified Compound [III]-(25))

To a suspension, in 150 ml of toluene, of 0.1 mole of t-octylphenoxy potassium produced according to the procedure of Synthetic Example 4 were added a solution of 26.6 g (0.1 mole) of [I]-(14) in 50 ml of N,N-dimethylacetamide and 0.1 g of cuprous chloride. The mixture was heated at about 80° C. for 2 hours while agitating. About 120 ml of toluene was distilled off under reduced pressure, and 200 ml of methanol was added to the reaction system, followed by cooling to about 10° C. and filtering the resulting crystals to obtain 35.4 g (yield 82%) of exemplified compound [III]-(25) as light yellow crystals. m.p. 146°–148° C.

SYNTHESIS EXAMPLE 8

(Synthesis of Exemplified Compound [III]-(28))

To a suspension of 0.1 mole of t-octylphenoxy potassium prepared according to the procedure of Synthetic Example 4 in 150 ml of toluene was a solution of 30.1 g (0.1 mole) of [I]-(21) in 50 ml of N,N-dimethylformamide, followed by heating on an oil bath at about 100° C. for 2 hours while agitating. About 100 ml of toluene was distilled off under reduced pressure, and 200 ml of methanol was added to the reaction solution, followed by filtering the resulting crystals to obtain 35.8 g (yield 76%) of exemplified compound [III]-(28) as yellowish brown crystals. m.p. 158°–161° C.

SYNTHESIS EXAMPLE 9

(Synthesis of Exemplified Compound [III]-(30))

A suspension of 30 g (0.1 mole) of a sodium salt of 4-dodecylthiophenol in 200 ml of tetrahydrofuran was prepared in the same manner as in Synthetic Example 6. Into the suspension was dropped a solution of 29.6 g (0.1 mole) of exemplified compound [I]-(16) in 50 ml of DMF. The reaction temperature was maintained at 50°–60° C. and agitation was continued for 1 hour. 200 ml of water was added to the reaction solution, followed by extraction twice with 200 ml of ethyl acetate. The extract was dried with Glauber's salt and the solvent was distilled off using an evaporator to obtain 51.8 g (yield 96%) of exemplified compound [III]-(30) as an oil. According to TLC, one spot was given. Attempts were made to crystallize the oil under various conditions, but no crystals were obtained. The structure was identified through mass spectroscopy and elementary analysis.

SYNTHESIS EXAMPLE 10

(Synthesis of Exemplified Compound [III]-(31))

4.9 g (0.2 mole) of exemplified compound [I]-(1) was added to 200 ml of morpholine, followed by heating on a steam bath for 8 hours. The reaction solution was cooled, to which 500 ml of water was added. The resulting crystals were filtered and washed with 350 ml of a 20% methanol solution, to obtain 69.5 g (yield 96%) of exemplified compound [III]-(31) as light brown crystals. m.p. 134°–135° C.

SYNTHESIS EXAMPLE 11

(Synthesis of Exemplified Compound [III]-(34) and [III]-(35))

34.2 g (0.24 mole) of 4-methylthiophenol and 16.1 g (0.24 mole) of potassium hydroxide were added to 350 ml of toluene and heated under reflux, followed by removing the resulting water using a water separator, thereby obtaining a potassium salt of 4-methylthiophenol. To the salt were added 67.1 g (0.244 mole) of exemplified compound [I]-(1) and 0.1 g of copper powder, followed by further heating for 2 hours under reflux. About 300 ml of toluene was distilled off under reduced pressure, and the concentrate was filtered under hot conditions, followed by adding 400 ml of methanol. The solution was cooled down to room temperature while agitating. The resulting crystals were filtered, washed with methanol, and dried to obtain 56.5 g (yield 62%) of 5-(4-methylthiophenoxy)-6-nitro-2-phenylbenzoxazole ([III]-(34)). m.p. 163°–165° C.

17 g (0.045 mole) of 5-(4-methylthiophenoxy)-6-nitro-2-phenylbenzoxazole was dispersed in 200 ml of methylene chloride, to which 23.3 g (0.095 mole) of m-chloroperbenzoic acid was added portion by portion under ice-cooling conditions. After the crystals had been once dissolved, fresh crystals again separated. After agitation for 1 hour, the crystals were filtered, followed by washing with an aqueous sodium sulfite solution, an aqueous sodium hydrogencarbonate solution, water and methanol and drying to obtain 18 g (yield 97%) of exemplified compound [III]-(35). m.p. 235°–242° C.

Other compounds [III] could be prepared according to the procedure of Synthetic Examples 4 through 11. The melting points of typical compounds are shown in Table 5.

TABLE 5

| Compound No. | m.p. (°C.) | Compound No. | m.p. (°C.) |
|---|---|---|---|
| [III]-(1) | 148–150 | [III]-(15) | 150–152 |
| [III]-(2) | 158–160 | [III]-(17) | 140–142 |
| [III]-(3) | 183–185 | [III]-(18) | 65–66 |
| [III]-(5) | 153–155 | [III]-(19) | (Oil) |
| [III]-(6) | 151–154 | [III]-(20) | 77–78 |
| [III]-(7) | 144–146 | [III]-(25) | 146–148 |
| [III]-(8) | 213–215 | [III]-(26) | (Oil) |
| [III]-(9) | 112–114 | [III]-(28) | 158–161 |
| [III]-(10) | 116–118 | [III]-(30) | (Oil) |
| [III]-(11) | 180–183 | [III]-(31) | 134–135 |
| [III]-(12) | 111–113 | [III]-(34) | 163–165 |
| [III]-(13) | 220–224 | [III]-(35) | 235–242 |
| [III]-(14) | 155–157 | [III]-(40) | 138–140 |

COMPARATIVE EXAMPLE 1

In order to show unexpectedly high usefulness of the substitution reaction of compounds [I] according to the invention, comparative tests using compounds, which are outside the scope of the invention, are described below.

By the operation on the scale of 1/10 of Synthetic Example 5, 0.1 mole of a potassium salt of 4-hydroxyanisole was obtained. To the reaction solution were added a solution of 21.2 g (0.1 mole) of 5-chloro-2-methyl-6-nitrobenzoxazole in 70 ml of DMF and 0.4 g of copper powder, followed by heating to about 85° C. The reaction solution immediately turned into a bluish purple color, whereupon crystals settled. Part of the crystals were taken out for confirmation of the structure, revealing formation of a polymeric by-product.

After the reaction over 3.5 hours, an insoluble polymeric compound was removed by filtration and the filtrate was extracted with etyl acetate, followed by distilling off the ethyl acetate to obtain about 6 g of a blackish brown solid matter. Silica gel chromatography was used for isolation to obtain 2.3 g (yield 7%) of a yellowish green substitution product. m.p. 84° C.

In the substitution reaction using, for example, 5-chloro-6-nitro-2-undecylbenzoxazole in which primary carbon atom is substituted at the 2 position of benzoxazole, or 2-anilino-5-chloro-6-nitrobenzoxazole substituted with an amino group having hydrogen atoms, there could scarcely be obtained substitution products in a manner similar to the case of Comparative Example 1. Instead, only the ring-opened product of oxazole or polymeric compound of an unknown structure was formed.

SYNTHESIS EXAMPLE 12

(Synthesis of Exemplified Compound [II]-(6))

500 ml of an aqueous solution of 80 g (2 moles) of caustic soda was added to a suspension of 181 g (0.5 mole) of exemplified compound [II]-(6) in 1.5 liters of ethanol. The reaction solution was gradually heated in a stream of nitrogen and refluxed for 2 hours. Thereafter, the reaction was cooled down to room temperature, to which 500 ml of water was added, followed by further adding concentrated hydrochloric acid added to such an extent that the pH of the reaction solution reached about 6–7. The reaction solution was cooled to about 15° C. and the resulting crystals were filtered to obtain 128 g (yield 93%) of exemplified compound [II]-(6) in the form of reddish orange crystals. m.p. 198°–199° C.

SYNTHESIS EXAMPLE 13

(Synthesis of Exemplified Compound [II]-(14))

A solution of 11 g of sodium methoxide in 40 ml of methanol and 100 ml of water were added to a solution of 42 g (0.1 mole) of exemplified compound [III]-(25) in 300 ml of ethanol, followed by agitating at about 50° C. for 1 hour. To the reaction solution was added concentrated hydrochloric acid until the pH of the reaction solution reached 6–7, followed by collecting the resulting crystals by filtration to obtain 38 g (yield 87%) of exemplified compound [II]-(14) in the form of light yellow crystals. m.p. 230°–231° C.

SYNTHESIS EXAMPLE 14

(Through Process of Synthesizing Exemplified Compound [II]-(7) from Exemplified Compound [IV]-(11))

273 g (1 mole) of exemplified compound [IV]-(11) and 9.5 g (0.05 mole) of p-toluenesulfonic acid monohydrate were added to 800 ml of toluene and heated under reflux for 1 hour. During the heating, about 22 ml of produced water was distilled off. Thereafter, 500 ml of toluene was distilled off, and 80 ml of diglime was added to the reaction solution. The reaction solution was added to a suspension of 261 g (1 mole) of potassium salt of 4-t-octylphenol in 400 ml of toluene in an atmosphere of nitrogen, followed by diluting with 80 ml of diglime. The reaction solution was heated under reflux at 130° C. for 1.5 hours, during which 500 ml of toluene was distilled off under reduced pressure. To the reaction solution were added 800 ml of ethanol and 250 ml of a solution of 160 g (4 moles) of NaOH, followed by heating under reflux for 2 hours. The reaction solution was cooled down to room temperature, to which 500 ml of water and 100 ml of ethanol. Thereafter, concentrated hydrochloric acid was added so that the pH of the reaction solution was 5–6. The resulting crystals were filtered and washed with water to obtain 23 g (total yield 68%) of exemplified compound [II]-(7) as reddish orange crystals. m.p. 187°–189° C.

Various compounds [II] could be prepared according to the procedure as shown in Synthetic Examples 12, 13 and 14. The melting points of typical compounds are shown in Table 6 below.

TABLE 6

| Compound No. | m.p. (°C.) | Compound No. | m.p. (°C.) |
| --- | --- | --- | --- |
| [II]-(1) | 144–146 | [II]-(14) | 230–231 |
| [II]-(3) | 167–169 | [II]-(18) | 116–117 |
| [II]-(5) | 172–174 | [II]-(19) | 235 (decomposed) |
| [II]-(6) | 198–199 | [II]-(20) | 115–117 |
| [II]-(7) | 187–189 | [II]-(22) | 158–160 |
| [II]-(8) | 183–185 | [II]-(24) | 191–192 |
| [II]-(12) | 133–135 | [II]-(34) | 107–109 |
| [II]-(13) | 133–135 | | |

COMPARATIVE EXAMPLE 2

In order to show the specific effect of the oxazole ring-opening and hydrolyzing reaction under alkaline conditions according to the invention, the ring-opening and hydrolyzing reaction under acidic conditions as known in the art are described below.

400 ml (2 moles) of 5N hydrochloric acid solution was added to a suspension of 181 g (0.5 mole) of exemplified compound [III]-(7) in 1.5 liters of ethanol, followed by heating under reflux for 2 hours. Because the reaction was found to proceed only partially, the reflux was continued for further 3 hours. The reaction solution gradually turned black and tar-like substances were secondarily produced in large amounts. The reaction solution was cooled for crystallization, but no crystals of the intended compound [II]-(6) could not be obtained since by-products were formed in large amounts.

The above procedure was repeated at high temperatures using, instead of hydrochloric acid, other acids such as diluted sulfuric acid, phosphoric acid, hydrobromic acid, hydroiodic acid, acetic acid, formic acid and sulfonic acid and also using butanol instead of ethanol as the solvent. In all the cases, complicated reaction mixtures were formed and it was found difficult to isolate compound [II]-(6).

From the above, it will be seen that the ring-opening reaction of benzoxazole under ordinary acidic conditions is not suitable for obtaining compound [II]-(6) from compound [III]. However, that is achieved only by the ring-opening and hydrolyzing reaction under alkaline conditions according to the invention.

Having described specific embodiments of our bearing, it is believed obvious that various modifications and variations of our invention is possible in light of the above teachings.

What is claimed is:

1. A process for preparing 2-amino-5-nitrophenol derivatives which comprises the steps of:
   (1) subjecting a benzoxazole derivative of the formula (I) to a nucleophilic substitution reaction at the 5 position of the benzoxazole derivative

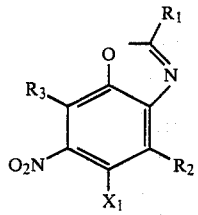

(I)

wherein $R_1$ represents a group bonding through a carbon atom having the number of substitution of hydrogen atoms of 0 or 1, or a group bonding through a hydrogen atom-free nitrogen atom, $R_2$ and $R_3$ independently represent a hydrogen atom or a group capable of substitution onto the aromatic ring, and $X_1$ represents a chlorine or bromine atom, thereby obtaining a corresponding benzoxazole derivative, and
   (2) opening the oxazole ring of the benzoxazole derivative to obtain a 2-amino-5-nitrophenol derivative of the formula (II)

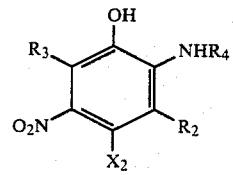

(II)

wherein $R_2$ and $R_3$ have, respectively, the same meanings as defined above, and $R_4$ represents a hydrogen atom or a $-COR_1$ group in which $R_1$ has the same meaning as defined above, and $X_2$ represents a nucleophilic group.

2. The process according to claim 1, wherein $R_1$ is a member selected from the group consisting of substituted phenyl, unsubstituted phenyl, substituted naphthyl, unsubstituted naphthyl, alkenyl containing up to 14 carbon atoms, lower alkynyl, tertiary alkyl containing 4 to 12 carbon atoms, secondary alkyl containing 3 to 15 carbon atoms, acyl containing 1 to 7 carbon atoms, carboxyl and ketimine having at most 7 carbon atoms.

3. The process according to claim 1, wherein $R_1$ is a group bonded through a hydrogen atom-free nitrogen atom.

4. The process according to claim 1, wherein $X_2$ is a nucleophilic group whose nucleophilic center is a hetero atom.

5. The process according to claim 1, wherein the oxazole ring of said benzoxazole derivative is opened by hydrolysis.

6. The process according to claim 5, wherein the ring-opening reaction is effected under alkaline conditions.

7. The process according to claim 1, wherein the ring-opening reaction is effected by hydrolysis under alkaline conditions.

8. The process according to claim 1, wherein $X_2$ of the 2-amino-5-nitrophenol derivative is selected from the group consisting of aryloxy, heterocyclic oxy, heterocyclic residue, arylthio and heterocyclic thio group.

9. The process according to claim 1, wherein $X_2$ of the 2-amino-5-nitrophenol derivative is an aryloxy group.

10. A process for preparing 2-amino-5-nitrophenol derivatives which comprises the steps of:
   (1) subjecting the compound of formula (IV) to a dehydration and ring closure reaction

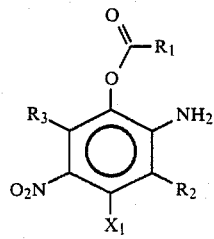

(IV)

wherein R₁ represents a group bonding through a carbon atom having the number of substitution of hydrogen atoms of 0 or 1, or a group bonding through a hydrogen atom-free nitrogen atom, R₂ and R₃ independently represent a hydrogen atom or a group capable of substituting onto the aromatic ring, and X₁ represents a chlorine or bromine atom;

(2) subjecting the resulting benzoxazole derivative of the formula (I) to a nucleophilic substitution reaction at the 5 position of the benzoxazole derivative, and

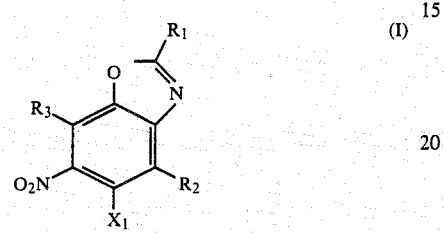

(3) opening the oxazole ring of the benzoxazole derivative to obtain a 2-amino-5-nitrophenol derivative of the formula (II)

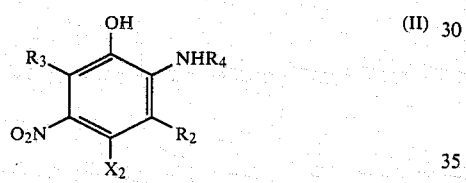

wherein R₂ and R₃ have, respectively, the same meanings as defined above, and R₄ represents a hydrogen atom or a —COR₁ group in which R₁ has the same meaning as defined above, and X₂ represents a nucleophilic group.

11. A process for preparing 2-amino-5-nitrophenol derivatives which comprises the steps of:

(1) subjecting the compound of the following formula to a dehydration and ring closure reaction

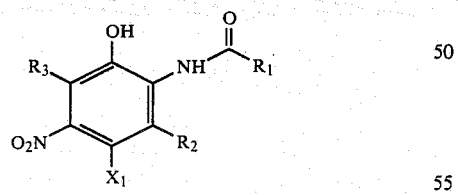

wherein R₁ represents a group bonding through a carbon atom having the number of substitution of hydrogen atoms of 0 or 1, or a group bonding through a hydrogen atom-free nitrogen atom, R₂ and R₃ independently represent a hydrogen atom or a group capable of substituting onto the aromatic ring, and X₁ represents a chlorine or bromine atom;

(2) subjecting a benoxazole derivative of the formula (I) to a nucleophilic substitution reaction at the 5 position of the benzoxazole derivative, and

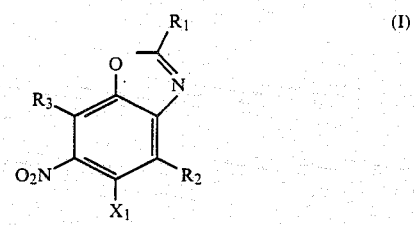

(3) opening the oxazole ring of the derivative to obtain a 2-amino-5-nitrophenol derivative of the general formula (II)

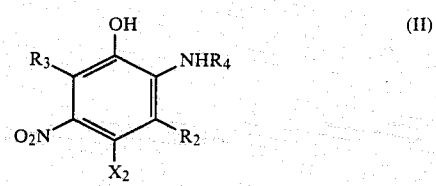

wherein R₂ and R₃ have, respectively, the same meanings as defined above, and R₄ represents a hydrogen atom or a —COR₁ group in which R₁ has the same meaning as defined above, and X₂ represents a nucleophilic group.

12. The process according to claim 1, wherein R₁ is a 5- or 6-membered saturated or unsaturated heterocyclic group which incorporates nitrogen, oxygen or a combination thereof.

13. The process according to claim 1, wherein R₁ is an alkenyl group containing 3 to 14 carbon atoms.

14. The process according to claim 1, wherein R₁ is an alkynyl group containing 2 to 3 carbon atoms.

15. The process according to claim 1, wherein R₂ and R₃ are independently selected from the group consisting of hydrogen, methyl, chlorine, bromine and methoxy.

16. The process according to claim 1, wherein R₂ and R₃ are independently selected from the group consisting of a halogen atom, an alkyl group, an alkenyl group, an aryl group, an alkoxy group, an aryloxy group, an acyloxy group, an amido group, a sulfonamido group, a ureido group, an alkyloxycarbonyl group, a carbamoyl group, a sulfamoyl group, a sulfonyl group, a sulfo group, a cyano group, and a heterocyclic residue.

17. A process for preparing 2-amino-5-nitrophenol derivatives which comprises the steps of:

(1) subjecting a benzoxazole derivative of the formula (I) to a nucleophilic substitution reaction at the 5 position of the benzoxazole derivative

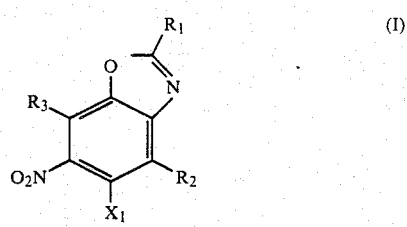

wherein R₁ represents a group bonding through a carbon atom having the number of substitution of hydrogen atoms of 0 or 1, or a group bonding through a hydrogen atom-free nitrogen atom, R₂ and R₃ independently represent a hydrogen atom or a group capable of substituting onto the aromatic ring selected from the group consisting of methyl, halogen, methoxy, alkyl, alkenyl, aryl, alkoxy, aryloxy, acyloxy, amido, sulfonamido, ureido, alkyloxycarbonyl, carbamoyl, sulfamoyl, sulfonyl, sulfo, cyano and heterocyclic, and $X_1$ represents a chlorine or bromine atom, thereby obtaining a corresponding benzoxazole derivative, and (2) opening the oxazole ring of the benzoxazole derivative to obtain a 2-amino-5-nitrophenol derivative of the formula (II)

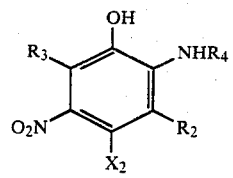

wherein $R_2$ and $R_3$ have, respectively, the same meanings as defined above, and $R_4$ represents a hydrogen atom or $COR_1$ group in which $R_1$ has the same meaning as defined above and $X_2$ represents a nucleophilic group.

* * * * *